United States Patent [19]

Ishida et al.

[11] Patent Number: 5,227,066
[45] Date of Patent: Jul. 13, 1993

[54] APPARATUS FOR SEPARATING LIVING CELLS

[75] Inventors: Masahiko Ishida; Ryoichi Haga; Harumi Matsuzaki, all of Hitachi, Japan

[73] Assignee: Hitachi, Ltd., Tokyo, Japan

[21] Appl. No.: 722,219

[22] Filed: Jun. 27, 1991

Related U.S. Application Data

[62] Division of Ser. No. 431,237, Nov. 3, 1989, Pat. No. 5,030,361.

[30] Foreign Application Priority Data

Nov. 10, 1988 [JP] Japan .................. 63-282544

[51] Int. Cl.$^5$ .................................... B01D 33/00
[52] U.S. Cl. .................. 210/360.1; 210/360.2; 210/364; 210/367; 210/368; 210/369; 210/374; 210/512.1; 422/72; 435/240.25; 435/240.46; 435/286; 435/312; 436/45; 436/177; 494/74; 494/75
[58] Field of Search .......... 210/787, 360.1, 360.2, 210/364, 367, 368, 369, 370, 372, 374, 380.1, 512.1; 422/72; 436/45, 177; 435/311, 312, 240.25, 240.46, 162, 286; 494/74, 75, 79, 37, 47, 67

[56] References Cited

U.S. PATENT DOCUMENTS

| | | | |
|---|---|---|---|
| 3,109,839 | 11/1963 | Keith, Jr. .................. | 494/74 |
| 3,168,474 | 2/1965 | Stallman et al. .......... | 494/74 |
| 3,536,253 | 10/1970 | Anderson et al. ......... | 494/74 |
| 3,708,111 | 1/1973 | Sheeler et al. ............ | 494/74 |
| 3,817,449 | 6/1974 | Westberg et al. .......... | 494/47 |
| 4,939,087 | 7/1990 | Van Wie et al. ........... | 210/787 |
| 4,988,623 | 1/1991 | Schwarz et al. ........... | 435/311 |
| 4,997,575 | 3/1991 | Hultsch .................... | 210/368 |
| 5,024,647 | 6/1991 | Jubin et al. ............... | 494/37 |
| 5,030,361 | 7/1991 | Ishida et al. .............. | 210/787 |

FOREIGN PATENT DOCUMENTS 62-266151 11/1987 Japan .

OTHER PUBLICATIONS

Hitachi Review, vol. 4, pp. 13–17 (1987).

*Primary Examiner*—Robert A. Dawson
*Assistant Examiner*—Sun Uk Kim
*Attorney, Agent, or Firm*—Antonelli, Terry, Stout & Kraus

[57] ABSTRACT

A centrifugal separation method for living cells is disclosed in which a cell containing solution is charged in a rotor chamber confined by a steam pressure-resistant wall. A rotor having septa is disposed in the rotor chamber. The septa are rotatable in the same direction at the same angular velocity as the rotor while at least part thereof is immersed in a solution in the rotor when cells are to be centrifuged from the cell-containing solution. After the cells are separated and adhered to the inner surface of the rotor, a supernatant in the rotor is discharged form the rotor. Then a fresh cultivating medium is introduced into the rotor, and the septa and the rotor are rotated at mutually different angular velocities while at least part of the septa is immersed in the fresh medium in the rotor. As a result, the cells are again suspended in the fresh medium.

6 Claims, 6 Drawing Sheets

APPARATUS FOR SEPARATING LIVING CELLS

This is a division of application Ser. No. 431,237, filed Nov. 3, 1989 now issued U.S. Pat. No. 5,030,361.

BACKGROUND OF THE INVENTION

1. Field of the Invention

This invention relates to a method for separating cells from a living cell-containing solution and more particularly, to a centrifugal separation method which eliminates damage to living cells and which provide cells free from contamination by bacteria.

2. Description of the Prior Art

Unlike bacterial cells, the propagation rate of animal cells is low and it is rather difficult to conduct continuous culture of a chermostat type. In order to culture industrially animal cells and to produce products, it is necessary to employ so-called "perfusion culture" which exchanges a liquid medium containing nutrient components with a waste liquor containing waste components while the cells are collected inside a culture tank. To keep the propagation of the cells by the perfusion culture, the cell separation must be repeated for a long period of time, such as at least one month, avoiding mechanical damage to the brittle cells under physiological conditions suitable for cells and a bacteria-free condition.

As described, for example, in "Hitachi Review", Vol. 4 (1987), p.p. 13-17, the manual separation operation has generally been employed in the past. In other words, a culture solution is charged in a centrifugal tube while paying the utmost caution so as not to cause bacterial contamination in a sterile chamber, then the cells are separated by an open type centrifugal apparatus. Then a supernatant is discarded, followed by suspending the deposited cells into a fresh medium and the cells are returned to the culture tank. This operation involves an extremely high risk of microbial contamination, and must be carried out by dividing the solution into small amounts. Since at least 1 or 2 hours is necessary for one batch, the cells are unavoidably placed, in the interim, under non-physiological conditions such as lack of dissolved oxygen, the drop of temperature, and the like.

Recently, a centrifugal apparatus of the sealed system type has been developed as disclosed, for example, in Japanese Patent Laid-Open No. 266151/1987 in order to separate blood and serum in hospitals. However, since the cell-containing solution comes into contact with a solid surface at a high speed and since a mechanical seal is employed while a rotary shaft penetrates through the outside, the brittle cells are likely to be damaged and there is the high risk of invasion of bacteria into the rotor chamber through the seal portion.

SUMMARY OF THE INVENTION

Object of the Invention

It is an object of the present invention to provide a centrifugal method which removes the drawbacks of handling of the cell suspension liquid such as found in the prior art described above, which does not permit the contact of the culture broth with a solid surface, but permits use of a rotor in a pressure-resistant sealed structure and which can suspend once again the separated and concentrated cells in a liquid medium.

Statement of the Invention

The present invention is concerned with a method of separating living cells by centrifugal force, which comprises: (1) supplying a cell suspension liquid into a rotor rotatably disposed in a chamber which is confined by a wall of a pressure vessel, said rotor being provided with septa which are rotatably disposed in said rotor independently from said rotor; (2) effecting separating the cells from the suspension liquid by centrifugal force due to the rotation of said rotor in the same direction as the rotating direction of said septa and in the same angular velocity as the angular speed of said septa, thereby to precipitate the cells on the inner surface of the wall of said rotor; (3) discharging a resulting supernatant from said rotor, while the precipitated cells are held on the surface of the wall; and (4) supplying a new medium solution for suspending cells into said rotor.

The present invention provides a method of separating cells which further comprises suspending the cells in the liquid medium by rotating said rotor and the septa at mutually different angular velocities, and discharge of the new cell suspension liquid from the pressure vessel.

The present invention employs a centrifugal apparatus featured in that a rotor is rotatably installed in a sealed rotor chamber of a steam pressure-resistant wall. The term "seal" does not mean a mechanical seal having a sliding portion but means a sealing system having high reliability of air-tightness in principle for the culture of cells for a long period, such as pressure contact between the chamber and a flange portion at the upper part of the chamber through a packing, for example.

According to this structure, invasion of bacteria into the rotor chamber from outside can effectively be prevented even in a continuous culture for a period as long as one month or more. Needless to say, the centrifugal apparatus in accordance with the present invention is made of a material having mechanical strength sufficient to withstand steam pressure sterilization conducted for that purpose.

The centrifugal apparatus is also featured in that a rotor and a tubular structure each having the following function are disposed in the rotor chamber. In other words, the rotor is rotatably disposed in the sealed rotor chamber and septa are disposed in the rotor so that the septa are rotated in the same rotating direction and at the same angular velocity as the rotor while at least its part is immersed in a solution in the rotor at least when the cells are separated from a cell-containing solution, and either one of the septa and the rotor is fixed while at least its part is immersed into the solution in the rotor and the other is rotated, or both of them are rotated in the same or different directions at the different angular velocities when the cells recovered under the state where they adhere to the inner wall of the rotor by centrifugal separation are suspended once again in a fresh liquid medium.

According to the structure described above, it becomes easy to centrifuge and recover the cells in the cell-containing solution, and to suspend once again the recovered cells in a liquid medium such as a liquid culture medium. In this case, since the rotor and the tubular member rotate synchronously with each other at the time of centrifugal separation, the solid surface and the cell-containing solution do not come into contact with solid surface at a high speed as they do in the conventional centrifugal apparatus, and the cells can be separated without receiving mechanical damage.

Furthermore, unlike the conventional sealed type rotor, the present invention provides also the effect of preventing the cells in the rotor from entering the anoxia condition by bringing the oxygen-containing gas in the rotor chamber into contact with the liquid surface at the time of the supply of the solution into the rotor, the centrifugal separation and the suspension.

The centrifugal apparatus employed in the present invention is featured by the fact that the rotation of the rotor is effected by a magnetic force transmission mechanism disposed outside the rotor chamber, through the rotor chamber wall. According to this structure, the rotor can be rotated freely in the horizontal direction while the rotor chamber is kept sealed.

DETAILED DESCRIPTION OF THE INVENTION

Hereinafter, detailed explanation will be given by citing some of examples.

First of all, the rotor chamber as the first feature of the present invention will be explained.

Since the rotor chamber is provided with structures such as the rotor which come into contact with a cell containing solution, it must be kept under the state containing no bacteria, during the separation period. To this end, steam sterilization is conducted, using a rotor chamber which has steam pressure-resistance of at least 120° C. for at least 10 minutes. The rotor chamber must have a structure or must be made of a material such that those components such as ferrous ions which effect adversely the cells do not come into contact with the culture solution. Ordinarily, stainless steel is employed.

From the view point of handling, the rotor chamber can be divided into a plurality of segments. This can be accomplished, for example, by dividing the rotor chamber into an upper cover and a lower container portion, into an upper cover, a bottom plate and an intermediate-drum or dividing further the drum into a plurality of segments in tho horizontal direction.

The rotor chamber is provided with at least the rotor, the tubular structure with septa and a piping arrangement that penetrates through the wall of the rotor chamber and communicates with the tubular structure.

The rotor is cup-shaped having an opening at its upper part and can rotate freely in the horizontal direction while being supported at the bottom of the rotor chamber. The rotor may be an integral unit or may have a structure that can be divided into a plurality of units for easy handling. The shape of the rotor can be determined in accordance with the kind and concentration of the intended cell suspension and with the predetermined operation conditions. However, its diameter must be greater than the opening so that the liquid can be kept at its drum portion during the rotation.

The center bottom of the rotor is used for supporting the tubular structure and various structures are used depending on the structure and operation method of the selected tubular member as will be described later.

The tubular structure has a lower part which comes into contact with the bottom inside the rotor, septa above the lower part and a sliding portion above the septa which slide with the lower terminal of the piping arrangement that penetrates through the wall of the rotor chamber.

As described above, the septa are rotated in the same rotating direction and at the same angular velocity as the rotor at the time of centrifugal separation while the entire portion of the septa or its part is immersed into the solution in the rotor. As will be described later, the rotation of the rotor is effected by the magnetic force through the bottom wall of the rotor chamber. The connection of the tubular structure and the rotor at the time of centrifugal separation can be accomplished by a clutch mechanism between the rotor and the tubular structure or by a rotation mechanism.

The clutch mechanism between the rotor and the tubular member is formed sometimes between the inner bottom portion of the rotor and the lower part of the tubular member or between the pipe portion at the upper part of the septa and the wall of the rotor chamber at other times.

On the other hand, when the cells recovered by the centrifugal separation are suspended in the medium solution, the rotor is rotated while the septa are kept fixed or the septa and the rotor are rotated in the same direction but at mutually different speeds or both of them are rotated in the mutually different directions. In this instance, the clutch that is operated at the time of centrifugal separation is disconnected from the tubular structure thereby to operate them independently of each other. The clutch can be cut off, for example, by moving slightly the tubular structure in the vertical direction to disengage the clutch engagement portion. Alternatively, the tubular structure may be fixed independently by a driving mechanism different from the driving mechanism of the rotor.

Incidentally, the tubular structure and the piping arrangement penetrating through the rotor chamber must be in communication for the liquid transfer from the rotor. Liquid transfer to the rotor such as feeding of culture solution or fresh medium can be made through the tubular structure. Therefore, part of the piping arrangement is composed of a flexible structure and at the same time, a rotary sliding surface is formed between it and the lower part of the piping arrangement in order to secure the flow the path with the penetrating piping arrangement even when the tubular structure moves up and down or rotates.

A heat-resistant and water-proofing material such as a silicone rubber pipe can be used for the flexible portion.

The septa may be sheet-like vanes, or a flexible member or a brush-like portion having a scraping function may be added to the end portion of the vane in order to promote suspending of the cells. The shape and number of vanes may be selected suitably in accordance with the rotor structure and its operating conditions. At times, bubbles occur and remain on the liquid surface at the time of introduction of the solution into the rotor or at the time of cell suspension. In such a case, a net coated with a defoaming agent or a net-like structure made of a defoaming material may be added to the upper part of the septa or to the opening of the rotor for the purpose of defoaming.

Various structures can be selected as the clutch mechanism between the tubular member and the rotor. For example, a clutch serves as the bearing for the tubular structure at the lower part of the rotor and the clutch can be equipped with a corrugated surface meshing with the lower part of the tubular structure. It is possible to dispose a cam on either of the lower part of the tubular structure ant the lower part of the rotor and a retractile cam meshing with the cam only at the time of unidirectional rotation, on the other. Furthermore, it is possible to employ a method which causes magnetic force to act between them. For example, the combinations of one of them made of a permanent magnet or an electromagnet with the other made of the permanent magnet, the electromagnet or a magnetic metal are used. When the electromagnet is used, the clutch is opened and closed by an electric wiring from outside the rotor chamber but in the case of the permanent magnet, a driving portion for moving up and down the tubular structure must be disposed separately for opening and closing the clutch.

A plurality of communication channels can be formed on the side surface of the clutch portion at the inner bottom of the rotor in order to make smooth the communication of the gas and the liquid between the tubular structure and the inside of the rotor.

The following systems are selected suitably as the sliding portion to be formed between the piping arrangement penetrating through the rotor chamber and the tubular structure, in accordance with the operational conditions, and the like.

In the systems, the cut surfaces or both ends to a ball joint type are usable as the sliding surfaces. These sliding surfaces or path near the sliding surface can extend and contract in the vertical direction in order to keep air-tightness as the piping arrangement with respect to the vertical movement of the tubular structure. For instance, a method which uses a flexible pipe material for part of the penetrating piping arrangement or for part of the tubular structure, a method which uses a double pipe structure for the sliding portions of both of them, and the like. Auxiliary means such as a spring or magnetic force may be used so that the sliding portions do not separate from each other but are always in mutual contact.

In the case of sliding by use of the double pipe system, a ring of a flexible material may be inserted into both gaps.

The tubular structure is supported in the vertical direction by the support structure from the rotor chamber. Since the tubular structure involves the rotation, a ball bearing or surface sliding mechanism is used for the support portion.

As described already, the rotor is rotated by the magnetic force transmission system through the bottom wall of the rotor chamber. Magnets are disposed at the rotor bottom and its opposite portion through the bottom wall in parallel with each other or one of them is the magnet with the other being a magnetic metal so as to rotate the latter and to rotate the rotor in the interlocking arrangement. A support from outside is necessary in order to freely rotate both of them around a vertical axis and to keep them fixed on the axis of rotation. For example, the rotor is supported by an arm equipped with a bearing that extends from the wall of the rotor chamber, while the opposite magnet is supported by an arm equipped with a bearing that extends from the wall of the motor chamber in the connected form with the motor.

The bottom wall of the rotor chamber may be a flat surface as a whole but its portion opposed to the magnet is curved inward so that the condensation inside the rotor chamber can be easily discharged from the rotating portion.

The rotating speed of the rotor is selected suitably in accordance with the operational conditions such as the centrifugal force, the operation time, and the like, but almost of cell strains can be adhere to the inner wall of the rotor, at least 5,000 G.

The rotating speed of the tubular structure, i.e. the relative rotating speed to the rotor at the time of cell suspension is lower than that at the time of centrifugal separation.

All the piping arrangements extending from the rotor chamber to the outside are those which can be sealed by valves. The piping arrangements include at least the piping arrangement for communicating the cell culture solution, the culture medium, the cell suspension, etc, into the rotor system and outside the system, the piping arrangement for discharging the drain in the rotor chamber and the piping arrangement for establishing the pressure balance between the outside of the system and the inner pressure of the rotor chamber. The former piping arrangement communicates with the bacteria-free system through a valve. The piping arrangement for discharging the drain is preferably double sealed by a valve in order to prevent invasion of bacteria. A filter capable of filtering bacteria in the external air is necessary for the latter piping arrangement in addition to the valve.

Furthermore, another piping arrangement may be added through a filter and a valve to the rotor chamber lest the cells in the rotor gets anoxia.

Next, the system including the centrifuge in accordance with the present invention and its operation process will be explained.

Figure 12:
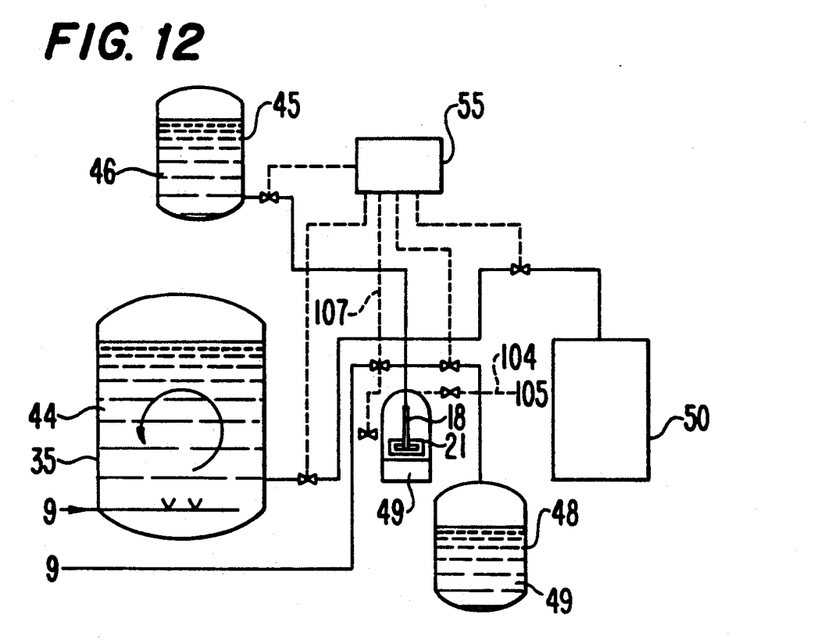
FIG. 12 shows the centrifugal separation system.

As shown in FIG. 12, the separation system comprises a cell containing solution tank 35, a medium tank 45 for suspending the cells, the centrifugal supernatant tank 48, and a steam generator 50 and piping arrangements from them are fitted to the tubular member penetrating through the rotor chamber wall. At least one valve or pump or both of them are disposed in each piping arrangement and are opened and closed by a process sequencer 55.

The inside of the rotor chamber is steam sterilized by the following process before the cell separation.

(1) introduction of steam into the rotor chamber through the tubular member;
(2) discharge of the air in the rotor chamber to the outside;

(3) closing of the drain discharge valve and the system is kept at 120° C. or above for at least 10 Minutes;
(4) cooling;
(5) discharge of the drain to outside the rotor chamber;
(6) introduction of sterile air into the rotor chamber and balancing of the inner pressure of the rotor chamber with external pressure; and
(7) control of the inner temperature of the rotor chamber to the predetermined temperature.

The steam sterilization operation can be conducted sufficiently by the manual operation.

Next, the cell separation is carried out by the following process:
(1) quantitative supply of the cell containing solution (culture solution) into the rotor through the tubular structure;
(2) centrifugal separation by the rotation of the rotor with the septa and the tubular structure;
(3) stop of the rotor;
(4) discharge of the supernatant outside the rotor chamber through the tubular structure;
(5) introduction of the medium liquid (liquid medium) into the rotor through the tubular structure;
(6) rotation of the rotor and the tubular structure at relatively different speeds to suspend the cells in the medium;
(7) return of the cell suspension into the cell containing solution tank (culture tank) through the tubular structure; and
(8) standing-by.

The process described above can be repeated. After the discharge of the supernatant to the outside of the rotor chamber at the step (4), the process may be returned to the supply of the cell containing solution into the rotor as the step (1) and after this operation is repeated several times, the process may then proceed to the steps (5) et seq.

At the supernatant discharge step (4), pressurized bacteria-free air may be supplied into part of the piping arrangement for supplying the cell containing solution into the rotor of the step (1) and the culture containing solution staying in the piping arrangement may be transferred into the rotor lest the culture containing solution staying in the piping arrangement is as such discharged outside the system together with the supernatant at the supernatant discharge step (4).

Furthermore, a plurality of centrifugal apparatus may be used for cell suspension such as a single culture tank or a single centrifugal apparatus may be used commonly for a plurality of culture tanks.

EXAMPLES

Some examples of the present invention and comparative examples will be explained in detail.

EXAMPLE 1

Figure 1:
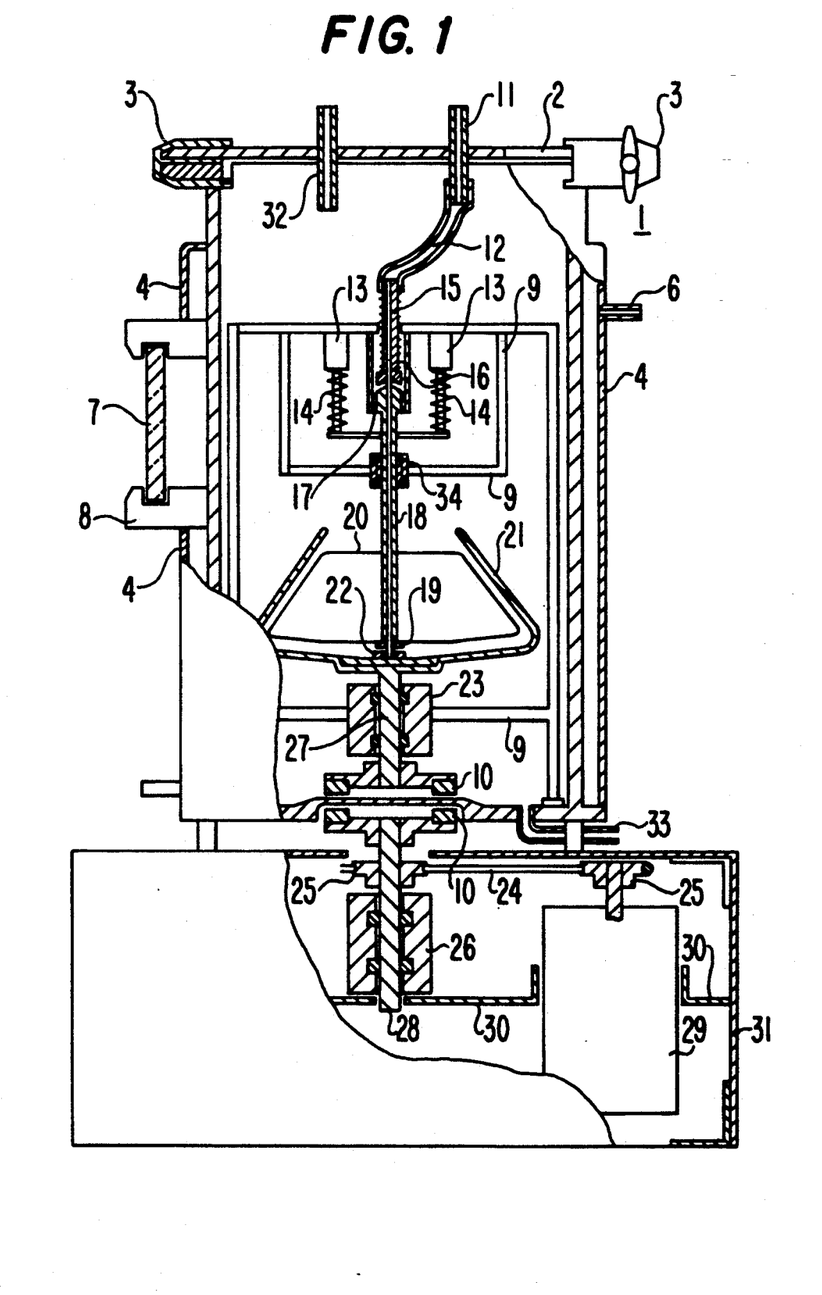
FIG. 1 is a sectional view of the centrifugal separation apparatus in accordance with the present invention.

FIG. 1 shows a typical example of the centrifugal apparatus in accordance with the present invention.

The apparatus uses a cylindrical pressure-resistant container made of a stainless steel and having a pressure resistance of 3.0 kg/cm$^2$ and is disposed with a rotor 21, a tubular structure 18 and a support 9 as main structural members. An external jacket 4 capable of passing thermostat water and an inspection window 8 having glass 7 for inspecting the rotor are provided on the side surface of the rotor chamber 1. An upper cover 2 is formed by a clamp band 3 so that the upper part of the rotor chamber is removable, and a gas-liquid transfer piping arrangement 11 for gas-liquid communicates with the tubular structure 18 and a gas transfer piping arrangement for balancing a pressure with an external pressure of the system after steam treatment penetrate through the upper cover 2.

The rotor 21 of this example has a trapezoidal sectional shape so that the cells accumulate at the acute angle corner portions of the bottom at the time of centrifugal separation (maximum liquid quantity of 500 ml at the time of centrifugal separation). The rotor is made of a corrosion-resiszant and steam-resistant material such as a stainless steel in the same way as the rotor chamber. The bottom of the rotor is connected by a rotary shaft 27 fixed by bearing 23 which is supported by the support 9, and by a permanent magnet 10 fitted below the bearing. The rotor shaft can freely rotate in a horizontal direction in the interlocking arrangement with a rotating magnetic field outside the rotor chamber. The permanent magnet in the rotor chamber is disposed at a position opposite to the permanent magnet 10 outside the bottom of the rotor chamber while interposing the bottom wall of the rotor chamber between them. The bottom wall of the rotor chamber between both magnets curved outwardly so as to increase the magnetic force and to make drain easily discharged. The permanent magnet 10 of the rotor chamber 31 is supported by a support 30 and by a bearing 26 and is connected to a motor 29 by a shaft 28, a pulley 25 and a belt 24. Rotor chamber 31 is provided with gas conduit 32 and and drain conduit 33.

The rotor 21 can be freely connected to the tubular structure 18 by a bottom clutch 22 in the rotor at the bottom of the rotor. The tubular structure descends at the time of centrifugal separation and is connected to the clutch 22 through its meshing gears 19, while it rises by the height corresponding to the gears at the time of suspending cells and is cut off from the rotor. A plurality of communication channels 85 are formed on the side surface of the clutch 22 at the bottom of the rotor in order to make easy the movement of a fluid in the tubular structure 18 and the rotor.

The tubular structure 18 has four vane-like septa 20 connected thereto and the upper part of the tubular structure is fixed by a bearing 34 for supporting the tubular structure, which bearing is fixed by the support 9. A lubricating portion 17 at the upper part of the tubular structure and a lubricating portion 15 opposite to the tubular structure together form a ball joint portion having high air-tightness by a spring 16 for close contact of lubricating surfaces and a spring 14 for pulling up and buffering the tubular structure. In order to raise the tubular structure 18 at the time of cell suspension, a solenoid 13 connected to the tubular structure 18 is employed.

A gas and liquid transfer piping arrangement 11 and the lubricating portion 15 opposite to the tubular structure are connected by a silicone rubber tube 12 for buffering the rise of the tubular structure 18.

EXAMPLE 2

Figure 2:
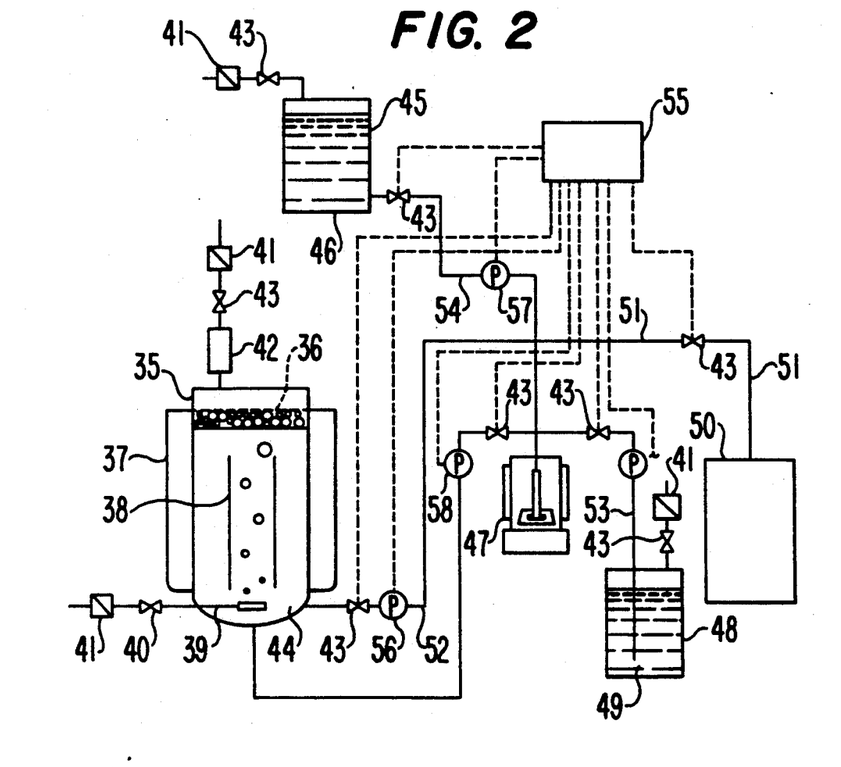
FIG. 2 shows a schematic diagram of the centrifugal separation system in accordance with the present invention.

A cell culture system is composed of several units by connecting the centrifugal apparatus 47, a culture tank 35, a medium tank 45, a centrifugal supernatant tank 48 and a steam generator 50 by piping arrangements as shown in FIG. 2. A valve 43 and a transfer pump are disposed at the intermediate portion of each piping arrangement between associated units and the centrifugal apparatus 47 and are connected electrically to a sequencer 55 for the sequence control of ON/OFF of each valve and each pump.

The culture tank 35 made of a stainless steel and provided with a jacket 37 has a working volume of 5 l and an oxygen-containing gas is sparged into the solution in the tank to dissolve oxygen into a culture broth 44. A draft tube 38 and a sparger 39 are disposed inside tie solution in the culture tank while a defaming layer 36 is disposed on the liquid surface.

An air filter 41 is connected via a valve 40, 43 to each of the culture tank 35, medium tank 45 and the centrifugal supernatant tank 48 in order to prevent invasion of bacteria from the environment. In this FIG. 42 designates a demister.

Before the start of culturing, steam was supplied from steam generator 50 via steam conduit 51 sequentially into each tank and each piping arrangement of the system to heat them at 125° C. for 30 minutes for sterilization. A medium 46 having the following composition was charged sterilely into the medium tank 45.

| Eagle MEM medium ("Eagle MEM Nissui 1, a product of Nisui Seiyaku K.K.) | 9.4 g/l |
|---|---|
| glutamine | 0.92 g/l |
| 7.5% aqueous sodium hydrocarbonate solution | 29 ml/l |
| glucose | 20 g/l |
| cow serum | 100 ml/l |

Rat liver cancer cell JTC-1 (Japan Tissue Culture No. 1) was used as the seed cell. The seed cell solution used for the culture was prepared in the following way.

Five milliliters of the medium described above was dividedly charged into each of 15 flat 20 ml flasks and after the JTC-1 strain described above was inoculated in a concentration of $1 \times 10^5$ cells/ml, then the culturing was carried out. The culturing was conducted at a temperature of 37° C. in an air atmosphere. The cells adhering to the flask surface after culturing for three days were peeled off and 75 ml of a culture solution having a cell concentration of $4.0 \times 10^5$ cells/ml was obtained. This culture solution was charged sterilely and dividedly into the centrifugal tube subjected to sterilization treatment, and the cells were recovered by a open suspension type centrifugal apparatus. The cells were inoculated into two 1-l roller bottles into which 75 ml of the medium was dividedly charged, and the culture was carried out at 37° C. for 3 days. The same operation was repeated several times to increase the concentration of the culture solution and to obtain 2l, of seed culture solution of $1.0 \times 10^5$ cells/ml. After this culture solution was introduced, 0.5l of the seed solution was inoculated to set the cell concentration to $4 \times 10^5$ cells/ml.

A stainless steel net having a rectangular mesh (one side of mesh: 3 mm) whose surface was coated by polysilane was placed as the defoaming layer, and oxygen-containing gas was sparged from ring spargers (pore diameter: 1 mm, 10 pcs) disposed at the bottom of the tank. Culturing was carried out at 37° C. The air quantity and the oxygen quantity were automatically controlled by adjusting the flow-rate of the oxygen-containing gas so that the dissolved oxygen concentration (DO) of the culture solution became 2.5 ppm. Carbon dioxide gas was added to the oxygen-containing gas and ventilated by a pH automatic adjustment device so that pH was controlled within the range of 7.0 to 7.6.

Next, 500 ml of the culture solution was transferred for one minute into the rotor of the centrifugal apparatus 47 by the pump 56 and the transfer piping arrangement 52. While the rotor 21 and the tubular structure 18 were kept connected, the rotor was rotated at 2,000 rpm for 2 minutes so as to separate and sediment the cells in the culture solution to the side wall of the rotor. After the rotation for 2 minutes, about 0.5 minutes was necessary before the rotor had stopped. After 0.5 minutes, the supernatant 49 in the rotor was transferred into the supernatant tank 48 by a pump and the transfer piping arrangement 53. Next, 500 ml of the liquid medium 46 was transferred from the medium tank 45 into the rotor by the pump 57 and the transfer piping arrangement 54 within one minute. Then, the tubular structure was pulled up by the solenoid and while it was disconnected from the rotor, the rotor was reversely rotated at 60 rpm for 0.5 minutes so as to disperse the cells into the medium. After stopping the operation of the rotor, the cell suspension in the rotor was sent back into the culture tank 35 by pump 58 through the cell suspension return piping arrangement. One cycle of the operations described above required 8 to 10 minutes. The operations were carried out 10 to 20 cycles per day and the culture was continued.

Table 1 shows the propagation state of the cells due to the culture described above.

As shown in Table 1, no rupture of the cells was observed at the time of cell separation and a high density state of $1.3 \times 10^7$ cells/ml, was reached within a short period and with a high survival ratio of 90% or more. In the interim, no bacterial cells were detected at all in the culture solution and it was evidenced that the bacteria-free condition could be maintained sufficiently.

COMPARATIVE EXAMPLE 1

The culture experiment was carried out in the same way, as in Example 2 by replacing the centrifugal apparatus used in Example 2. The centrifugal apparatus used in this Comparative Example has the following difference in the rotor from the centrifugal apparatus used in Example 1.

1) The upper part of the rotor of Example 1 is closed.
2) As the rotation transmission mechanism of the rotor, the rotor bottom and the motor shaft are directly coupled.
3) Inlet/outlet pipes for the liquid are fixed and the rotor keeps air-tightness with the liquid inlet/outlet pipes through a mechanical seal.
4) The size of the septa for suspending the centrifuged cells in the medium is reduced and is mounted below the liquid transfer piping arrangement.

The operation was carried out in the same way as in Example 1 except that connection/disconnection between the tubular structure 18 and the rotor 21 in Example 1 was not effected. The results of operations are shown in table 2. Since the cells came into contact with the septa fixed at the time of centrifuge and with the liquid inlet/outlet pipes at a high speed, the survival ratio dropped due to the rapture of the cells and culturing could not be carried out. Moreover, cell contamination, which was believed to result from the mechanical seal portion, occurred on the fifth day.

Next, in the following Examples 3 through 9, the basic structure inside the rotor chamber and its operation method at the time of centrifugal separation and cell suspension will be explained.

EXAMPLE 3

Figure 3A:
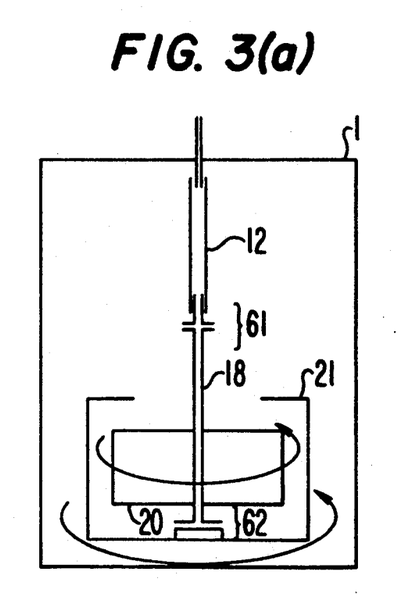
FIGS. 3a and 3b are sectional views of the centrifugal separation apparatus in accordance with the present invention.
Figure 3B:
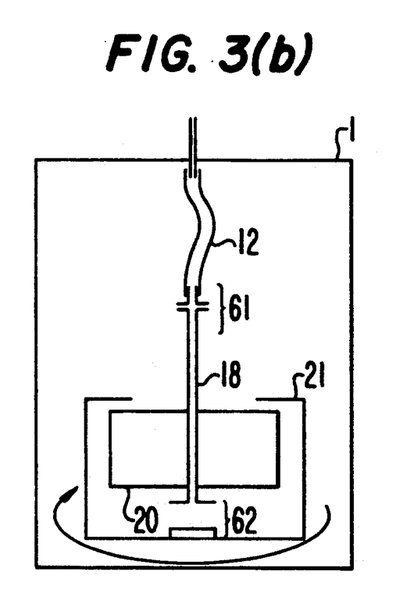

Example 3 is shown in FIGS. 3a and 3b. FIG. 3a shows the operation mode in the centrifugal separation and FIG. 3b shows the operation mode in the cell suspension.

The rotor chamber 1 is closed off from environment by a system pressure-resistant wall. A material of the wall is a heat-resistant, pressure-resistant and waterproofing material so that the rotor chamber 1, the mechanism inside the rotor chamber and the interior of the piping arrangement can withstand a temperature of at least 120° C. for at least 10 minutes. Toxic components such as heavy metal ions are not substantially eluted from the material. Examples of such materials are stainless steel and titanium. The rotor 21 is of a magnetic force transmission system, can freely rotate around the vertical axis and has a bowl-like shape having an opening at its upper part. The rotor 21 can be driven and rotated by the magnet through the bottom wall of the rotor chamber 1. The tubular structure 18 is fitted onto the rotary shaft inside the rotor 21. The lower end of the tubular structure 18 forms a clutch portion 62 capable of attaching and detaching to and from the bottom inside the rotor. The tubular structure 18 has the septa 20 above the clutch portion and inside the rotor chamber and its upper end forms a sliding surface with the lower end of the piping arrangement penetrating through the upper part of the rotor chamber. The intermediate portion of the penetrating piping arrangement uses a flexible tubular structure 12.

TABLE 1

| culture time (day) | 0 | 1 | 2 | 3 | 5 | 10 | 20 | 30 | 40 |
|---|---|---|---|---|---|---|---|---|---|
| culture condition | | | | | | | | | |
| centrifugal separation (cycles/day) | — | | | 10 | | | 20 | | |
| quantity of medium exchange (l/day) | — | | | 5 | | | 10 | | |
| living cell concentration ($\times 10^3$ cells/ml) | 4.0 | 4.0 | 4.5 | 7.0 | 11 | 32 | 106 | 120 | 130 |
| survival ratio (%) | 93 | 95 | 96 | 96 | 96 | 96 | 95 | 96 | 96 |
| detected bacteria | | | | | Nil | | | | |

TABLE 2

| culture time (day) | 0 | 1 | 2 | 3 | 5 | 10 |
|---|---|---|---|---|---|---|
| culture condition | | | | | | |
| centrifugal separation (cycles/day) | — | | | | 10 | |
| quantity of medium exchange (l/day) | — | | | | 5 | |
| living cell concentration ($\times 10^3$ cells/ml) | 4.0 | 0.2 | 0.1 | ≦0.01 | ≦0.01 | ≦0.01 |
| survival ratio (%) | 93 | 2.3 | 0.52 | — | — | — |
| detected bacteria | | | Nil | | rod-shaped bacteria | propagation of rod-shaped bacteria |

Before the centrifugal-separation, the culture broth containing the cells introduced from the culture tank into the rotor through the flexible piping arrangement 12, the lubricating portion 61 and the tubular structure 18. Next, while the tubular structure 18 is coupled with the rotor at the clutch portion 62 at its lower end, penetrates through the rotor chamber at its sliding portion 61 and slides at the lower end of the fixed piping arrangement, it rotates in the same direction at the same speed as the rotor, and the cells in the culture solution are centrifuged onto the inner surface of the drum of the rotor 21. After the stop of the rotor 21, the supernatant is discharged outside the rotor chamber through the tubular structure 18. Next, after the liquid medium is introduced into the rotor chamber through the tubular structure 18, it is pulled up and disconnected from the rotor so that at least the entire portion of the septa 20 does not come out on the liquid surface. While the tubular structure 18 is kept disconnected from the rotor and while it forms the lubricating portion, it can move upward due to the deformation of the flexible piping arrangement 12. Next, the tubular structure 18 is fixed and the rotor 21 is rotated reversely in order to suspend the cells on the rotor inner wall into the liquid medium.

EXAMPLE 4

Whereas the tubular structure 18 is fixed and the rotor 21 is rotated reversely at the time of cell suspension as in Example 1, the rotor was rotated in the same direction at the time of centrifugal separation in this Example.

EXAMPLE 5

This Example is different from Example 1 in the mechanism of the clutch portion 62. Whereas the clutch at the lower part of the tubular structure faces downwardly and the clutch surface of the rotor bottom surface faces upwardly in Example 1, the backs of both clutch surfaces in Example 1 form the clutch surface in this Example while the lower part of the tubular member penetrates through the center of the clutch surface of the rotor bottom surface as shown in the drawing.

The tubular structure 18 is fixed and the rotor is rotated reversely at the time of cell suspension. It is also possible to fix the tubular structure 18 and to rotate the rotor in the same direction as the direction at the time of centrifugal separation, when the cell suspension is carried out.

EXAMPLE 6

Unlike Example Nos. 1 through 4, the clutch portion 62 in this Example consists of an electromagnetic clutch or a clutch equipped with a reverse rotation check pin. Therefore, centrifugal separation and cell suspension can be made without moving down the tubular structure 18 up and down. The rotor 21 and the tubular structure 18 are coupled by the clutch portion 62 of the mechanism described above at the time of centrifugal separation, the clutch portion (not shown) disposed at the intermediate portion of the tubular structure 18 is kept open and the rotor and the tubular structure rotate synchronously with each other.

The clutch portion 62 is cut off at the time of cell suspension but since the clutch portion operates and the tubular structure 18 is fixed, only the rotor rotates and the cells are suspended in the liquid medium.

EXAMPLE 7

The rotation mechanism of the tubular structure 18 disposed separately from that of the rotor, is rotated synchronously with the latter at the time of centrifugal separation and is rotated reversely with respect to the rotor at the time of cell suspension.

In this case, it is possible to stop the tubular structure 3 by utilizing the resistance of the rotation mechanisms 8, 9 of the tubular structure 18 and to rotate reversely on the rotor.

EXAMPLE 8

The rotor 21 and the tubular structure 18 have different rotation driving portions, and the rotating directions of the rotor 21 and tubular structure 18 are made opposite to each other at the time of cell suspension. In this case, the rotor 21 and tubular structure 18 are rotated in the same rotating direction but at relatively different rotating speeds.

EXAMPLE 9

The clutch portion between the rotor 21 and the tubular structure 18 in Example 6 is removed and the clutch portion 62 is disposed on the intermediate portion of the tubular member so that the tubular structure 18 is rotated in the same direction and at the same speed as the rotor by use of an exclusive driving source at the time of centrifugal separation. The tubular structure 18 is fixed by the clutch at the time of cell suspension and only the rotor 21 is rotated.

Next, some examples relating to the basic structure of the rotor chamber 1 will be illustrated.

EXAMPLE 10

Figure 4:
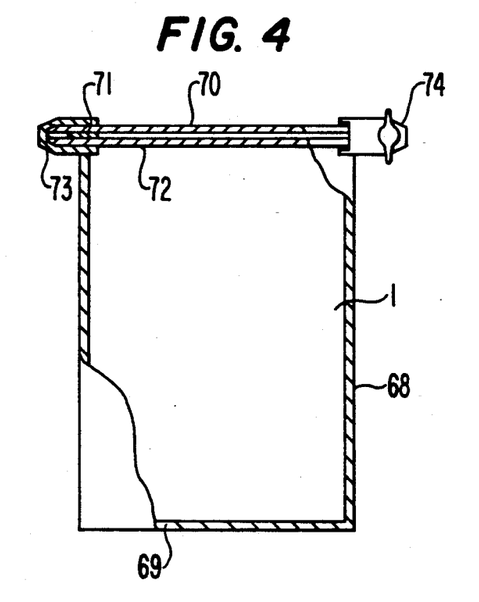
FIG. 4 is a sectional view of a rotor chamber.

The rotor chamber 1 is divided into the upper surface wall 70 of the rotor chamber and the side surface wall of the rotor chamber forming the lower part of the rotor chamber as shown in FIG. 4. The upper surface wall 70 of the rotor chamber and the lower part of the rotor chamber are made air-tight by both flanges 70 and 72 using a packing 71 as a sealing material. In the drawing, both flanges are shown clamped by fastening a flange clamp band 73 by a fastening screw 74.

EXAMPLE 11

The rotor chamber 1 is divided into the upper surface wall 70 of the rotor chamber, the side wall 68 of the rotor chamber and the bottom surface wall 69 of the rotor chamber. Coupling of the upper and lower surface walls 70 and 69 is made by the same mechanism as that of the upper surface wall 70 of Example 10.

The upper surface wall 70 and lower surface wall 69 of the rotor chamber 1 can be coupled to the flange 72 of the side wall 68 of the rotor chamber by coupling the flange 72 by a bolt and a nut while interposing the packing 71.

EXAMPLE 12

The rotor chamber is further divided at the intermediate portion of the side surface wall 2 in Example 11.

Next, some examples of the rotor will be illustrated.

EXAMPLE 13

Figure 5A:
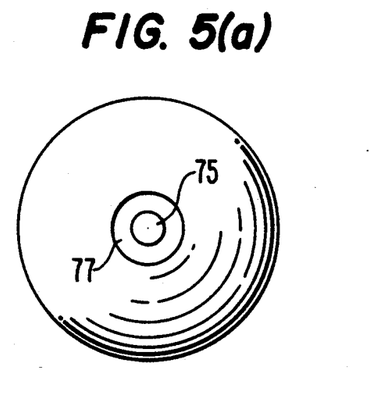
FIGS. 5a and 5b are a plane view and a sectional view of a rotor.
Figure 5B:
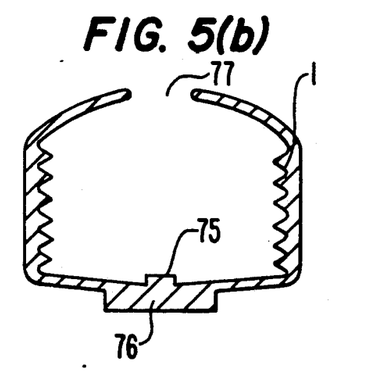

FIGS. 5a and 5b shows a plane view and a sectional view of the rotor whose inner face is of wave form. The rotor has a receptacle 75, a shaft connecting portion 76 and an opening 77. In this case, cells which are easily peeled off from the surface of the rotor wall can be retained on the waved-shaped wall.

In order to keep air-tightness of the contact surfaces of upper and lower halves when the rotor is divided into them, the rotor wherein the packing is inserted between both of them.

In the rotor which can be divided into the upper and lower portions, the rotor wherein the contact surfaces between both portions are fixed by a screw or by fastening by use of a band. The sectional shape of the rotor may be jar-shaped, diamond-like, or substantially equilateral triangle.

The rotor forming a plurality of rack-like stages from the inner side surface of the rotor is towards the direction of the rotary shaft. These stages can be made detachable with respect to the inner side surface of the rotor.

The sectional view of the rotor may also be substantially arcuate.

Next, some examples relating to the structure of the septa will be explained.

Figure 6A:
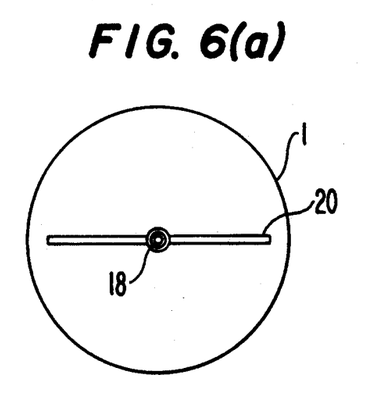
FIGS. 6a and 6b are a plane view and a sectional view of septa.
Figure 6B:
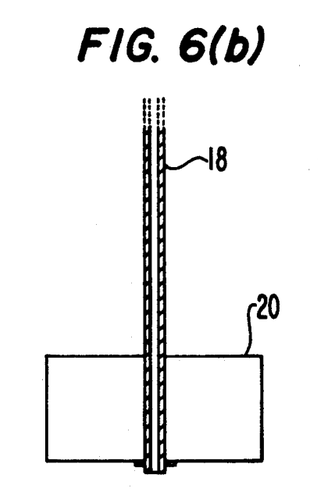

The septa shown in FIGS. 6a and 6b has two blades that extend from the tubular structure in the centrifuging direction.

Another type of septa may have four blades that extend from the tubular structure in the centrifugal direction. The number of blades may be an arbitrary number of at least three.

In another type of the septa, the septum is divided vertically into a plurality of stages.

The septa may be divided vertically into a plurality of stages and each of the divided septa has a mutually different shape.

The septa are equipped with a defoaming layer (such as a defoaming net) for breaking foams produced in the rotor, at the upper part of the septa.

Next, some examples of the clutch-mechanism between the lower end of the tubular structure and the bottom inside the rotor will be illustrated.

EXAMPLE 14

Figure 7:
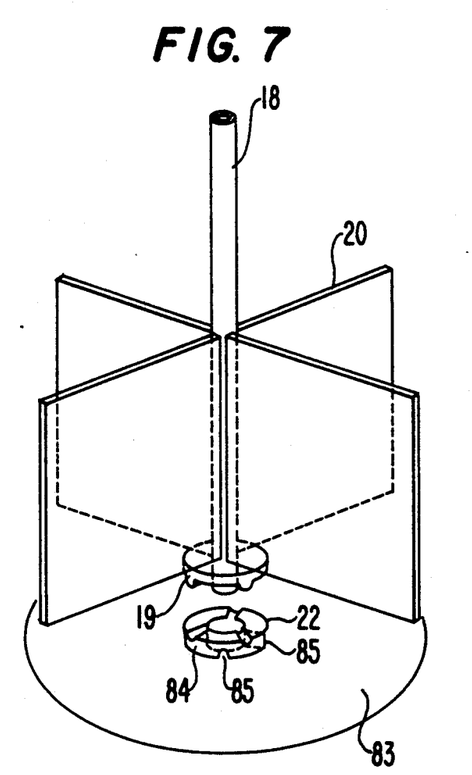
FIG. 7 shows clutch mechanism.

FIG. 7 shows the clutch having the mechanism wherein both of the surface of the center portion of the bottom 83 inside the rotor and the surface at the lower part of the tubular structure 18 form corrugations and coupling is attained and released when the tubular structure 18 moves up and down. This example shows the shape where the section of the corrugated portion has a curve. A gas-liquid communication channel 85 is formed at the lower part of the rotor so as to the communicate the gas and liquid that move up and down in the tubular structure.

The clutch may have an acute angle portion on the section of the corrugated portion of the clutch and having a small number of gears.

A large number of gears may be disposed on the clutch portion.

The clutch may use a permanent magnet, an electromagnet or a magnetic metal for the clutch portion at the lower part of the tubular structure and uses a permanent magnet at the clutch portion of the bottom of the rotor. The tubular structure in this mechanism moves up and down.

The clutch may also have the mechanism wherein the tubular structure does not move up and down, the lower part of the tubular structure forms a cam in the horizontal direction and the tubular structure and rotor are allowed to rotate integrally with each other in one direction but are inhibited to operate in the interlocking arrangement in the opposite direction by a reverse check pin disposed on the inner wall of the clutch portion at the bottom in the rotor facing the cam, in the horizontal direction.

The clutch may have the mechanism wherein the clutch at the lower part of the tubular structure and the bottom in the rotor relies on the cam mechanism disposed in the horizontal direction of both surfaces. A groove having a gradient of a desired depth is formed on one of both surfaces and a pin capable of moving up and down in formed on the opposed surface.

Next, some examples relating to the sliding lubricating portion at the upper part of the tubular structure will be illustrated.

EXAMPLE 15

The mechanism of the sliding lubricating portion wherein the lubricating surface at the upper end 17 of the tubular structure and the opposed lubricating surface 15 disposed on the former are horizontal and in parallel with each other, and at least part of the piping arrangement between the opposed lubricating surface and the upper wall of the rotor chamber consists of the flexible pipe 12.

The mechanism of the sliding lubricating portion may have the lubricating surface 15 at the upper end of the tubular structure and the opposite lubricating surface 17 positioned on the lubricating surface so that the surfaces 15, 17 are in parallel with each other but one of them forms cavities while the other forms convexes. In this examples, a bearing is disposed downstream of the lubricating surface and a spring is disposed near the lubricating surface in order to prevent deviation or fall-off of the tubular structure from the rotary shaft and to bring both lubricating surfaces into close contact with each other. A plurality of springs may be used, too.

In Example 15, the sliding lubricating portion may have a ball joint structure. In this case, the spring can be used near the lubricating surface(s).

The sliding lubricating portion may also cover the side surface at the upper end of the tubular structure. In this case, the spring(s) can be used near the sliding surface.

Figures 8A, 8B:
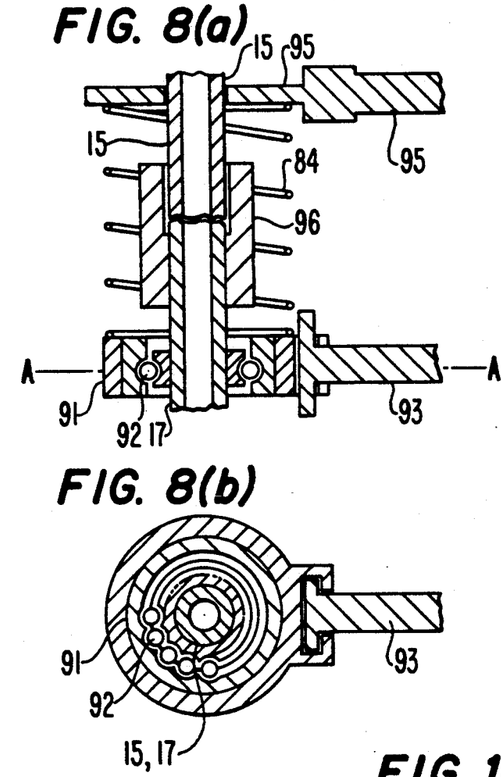
FIGS. 8a and 8b are a vertical sectional view and plane sectional view of a sliding lubricating portion.

FIG. 8a and 8b show the sliding lubricating portions wherein the lubricating surface of the tubular structure covers also the side surface of the opposed lubricating surface of the tubular structure. FIG. 8a shows a vertical sectional view and FIG. 8b shows a plane sectional view. In FIG. 8a, 84 designates a spring and 95 a support for lubrication. In FIGS. 8a and 8b, 91 is a rotary bearing, 92 is a ball bearing, 93 is a bearing support and 96 is a sleeve.

Figure 9:
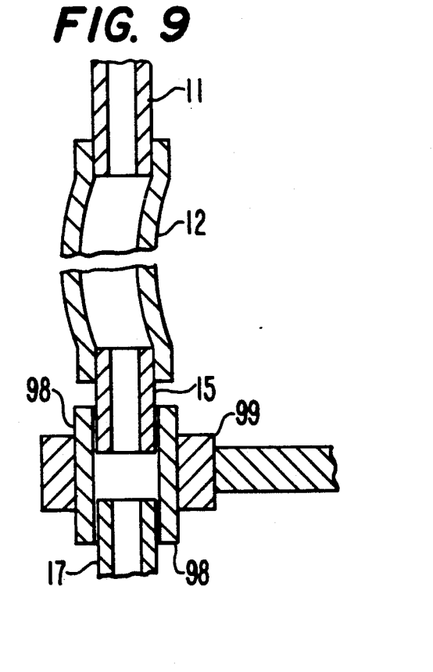
FIG. 9 shows the support mechanism of the rotor.

The upper end 17 of the tubular structure of the sliding lubricating portion, as shown in FIG. 9 may serve as an inner pipe while the opposed lubricating portion 15 serves as an output pipe and the side surfaces. In this FIG. 98 is a bearing and 99 is a support for the bearing.

The upper end of the tubular structure of the sliding lubricating portion may also serve as an inner pipe while the opposed lubricating portion 15 serves as an outer pipe, the side surfaces between both pipes are lubricated through an O-ring and this sliding lubricating portion is disposed on the flexible piping arrangement 12.

Next, some examples of the rotor support mechanism will be illustrated.

EXAMPLE 16

Figure 10:
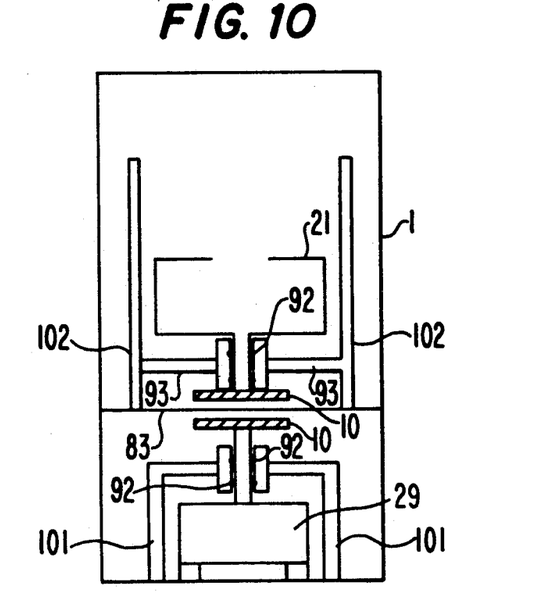
FIG. 10 shows the structure of a lower part of the rotor chamber.

The rotor 21 as further shown in FIG. 10, is supported by a bearing which is supported from the inner side surface of the rotor chamber while the rotary shaft of the magnet of the motor chamber is supported by a bearing supported from the side surface of the motor chamber. Each bearing may be a tandem bearing.

The bearing 92 of the support mechanism is supported from the bottom surface of the rotor chamber via support 102 and the bottom surface of the motor chamber via support 101.

The bearing of the support mechanism is supported from the bottom surface of the rotor chamber and the upper part of the motor chamber.

Next, some examples of the piping arrangement connected to the rotor chamber will be illustrated.

EXAMPLE 17

The piping arrangement system of the centrifuge includes a gas transfer piping arrangement 32 for attaining the balance with an external pressure after steam sterilization besides the gas-liquid transfer piping arrangement 11 connected from the rotor chamber to the tubular structure 18 and the drain discharge piping arrangement.

A bacteria-removing filter 41 for a ga is inserted into 32 to prevent invasion of bacteria into the rotor chamber.

Two valves 43, 43 are disposed in series in the drain discharge pipe of Example 17. If the valve is doubled, back-flow of the bacteria at the time of drain discharge can be prevented effectively.

A piping arrangement for introducing oxygen-containing gas is added in order to pass an oxygen-containing gas into the rotor chamber. Anoxia of the cells can be prevented effectively by passing sterile air and oxygen-rich gas while the cells stay in the rotor chamber.

Figure 11:
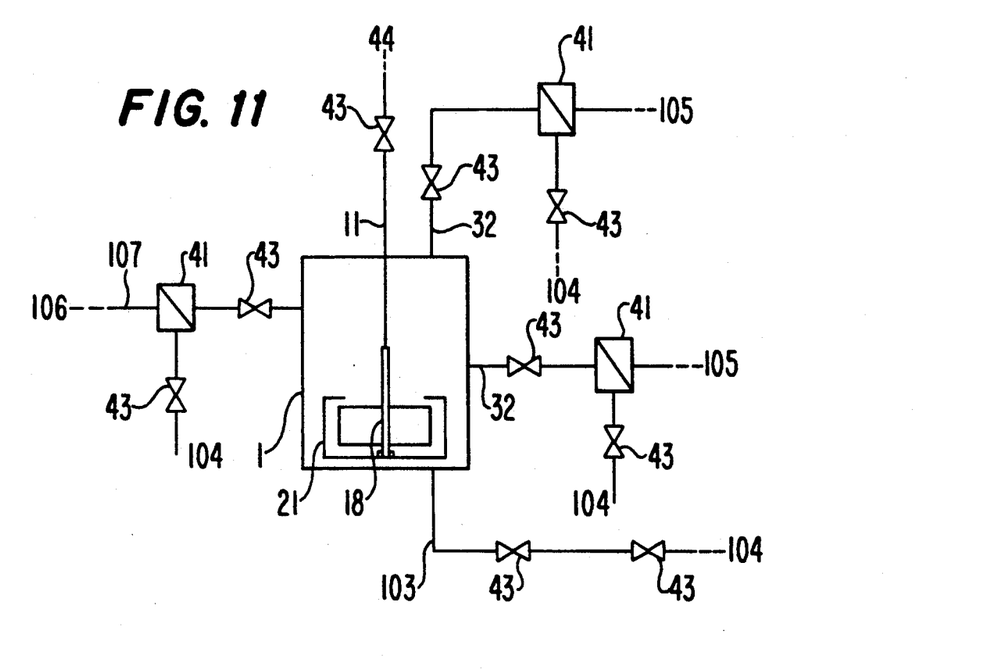
FIG. 11 shows the piping arrangement of the centrifugal separation system.

As shown in FIG. 11, a gas transfer piping arrangement for discharging the exhaust gas due to ventilation of the oxygen-containing gas to the outside of the rotor chamber is exclusively disposed separately from the gas transfer piping arrangement for attaining the pressure balance after steam sterilization. In FIG. 11, reference numeral 1 indicates a rotor chamber, 11 a gas-liquid transferring pipe, 18 a tubular structure, 32 a gas discharging pipe, 41 a filter, 43 a valve, 44 a centrifugal supernatant cell suspended solution, 103 a drain discharging pipe, 104 a drain, 105 a discharged gas or introduced gas, and 106 an oxygen-containing gas. In FIG. 11, 107 designates a conduit.

Next, some examples of the system including the centrifugal apparatus will be illustrated.

EXAMPLE 18

There is provided a system for conducting the process wherein the piping arrangement passing through the tubular structure 18 of the centrifugal apparatus and transferring the liquid outside the rotor connects at least the culture tank 35, the medium tank 45, the centrifugal supernatant tank 48 and the steam generator 50 to one another, and the valve and the pump that are inserted into the piping arrangement are subjected to opening/closing and ON/OFF control by the process sequencer 55.

FIG. 12 shows another example of the system for executing the process wherein a bacteria-free oxygen-containing gas introduction piping arrangement is connected to the rotor chamber in the piping arrangement mentioned above and the valve inserted into this introduction piping arrangement is opened and closed by the process sequencer 55 common to this system.

Next, the outline of the process by the system including the centrifugal apparatus of the present invention will be illustrated.

EXAMPLE 19

The following is the process flow. The following operations are carried out after steam sterilization of the rotor chamber and the piping arrangement.
(1) quantitative supply of the cell-containing solution from outside the rotor chamber into the rotor.
(2) centrifugal separation by integral rotation of the rotor and the tubular structure.
(3) stop of the rotor.
(4) discharge of the centrifugal supernatant to outside the rotor chamber through the tubular structure.
(5) quantitative supply of the cell suspension medium liquid into the rotor.
(6) the rotation of one of the rotor and the tubular structure or their rotation at mutually different speeds to suspend the cells in the liquid medium.
(7) discharge of the cell suspension solution to outside the rotor chamber through the tubular structure.
(8) stand-by.
(9) return to the step (1).

In place of the process mentioned above, there is provided the following process which is carried out after steam sterilization.
(1) quantitative supply of the cell-containing solution from the tubular structure into the rotor.
(2) centrifugal separation by the rotation of the rotor.
(3) stop of the rotor.
(4) discharge of the centrifugal supernatant from the tubular structure to outside the rotor chamber.
(5) return to the step (1) and the repetition of operations of at least twice.
(6) re-suspension of the cells by the rotation of the tubular structure and the rotor at the mutually different speeds.
(7) discharge of the cell suspension solution from the tubular structure to outside the rotor chamber.
(8) standing-by.
(9) return to the step (1).

what is claimed is:

1. An apparatus for separating living cells by centrifugal force, which comprises a pressure vessel; means for supplying a cell suspension liquid into a rotor rotatably disposed in said pressure vessel, said rotor being provided with septa which are rotatably disposed in said rotor independently from said rotor; means for effecting separation of the cells from the suspension liquid by centrifugal force due to the rotation of said rotor in the same rotating direction as that of said septa, and in the same angular velocity as that of said septa thereby to precipitate the cells on an inner surface of the wall of said rotor; means for discharging a resulting supernatant from said rotor, while the precipitated cells are held on the surface of the wall of said rotor; and means for supplying a new suspension liquid into said rotor.

2. An apparatus for separating living cells by centrifugal force according to claim 1, wherein the septa are provided with scraping means at an end portion of each septa to promote suspension of the cells.

3. An apparatus for separating living cells by centrifugal force according to claim 1, wherein the rotor has a wave-shaped wall.

4. An apparatus for separating living cells by centrifugal force, which comprises a pressure vessel; means for supplying a cell suspension liquid through a conduit into a rotor rotatably disposed in the pressure vessel, said rotor being provided with septa which are rotatably disposed in said rotor independently from said rotor; means for effecting separation of the cells from the suspension liquid by centrifugal force due to the rotation of said rotor in the same rotating direction as that of said septa, and in the same angular velocity as that of said septa, thereby to precipitate the cells on an inner surface of the wall of said rotor; means for stopping the rotation of said rotor; means for discharging a resulting supernatant from said rotor, while the precipitated cells are held on the surface of the wall of said rotor; and means for supplying a new suspension liquid into said rotor.

5. An apparatus for separating living cells by centrifugal force, which comprises a pressure vessel; means for supplying a cell suspension liquid through a conduit into a rotor rotatably disposed in a chamber which is gas-tightly confined by a wall of the pressure vessel, said rotor being provided with septa which are rotatably disposed in said rotor independently from said rotor; means for effecting separation of the cells from the suspension liquid by centrifugal force due to the rotation of said rotor in the same direction as the rotating direction of said septa, thereby to precipitate the cells on an inner surface of the wall of said rotor; means for discharging a resulting supernatant from said rotor through said conduit, while the precipitated cells are held on the surface of the wall; means for supplying a new liquid medium for suspending the cells into said rotor; and means for effecting suspension of the cells in said new liquid medium by rotating said rotor and said septa in different speeds in the liquid medium.

6. An apparatus for separating living cells by centrifugal force, which comprises a pressure vessel; means for supplying a cell suspension liquid into a rotor rotatably disposed in a chamber which is gas-tightly confined by a wall of the pressure vessel, said rotor being provided with septa which are rotatably disposed in said rotor independently from said rotor; means for effecting separation of the cells from the suspension liquid by centrifugal force due to the rotation of said rotor in the same direction as the rotating direction of said septa, thereby precipitating the cells on an inner surface of a wall of said rotor; means for stopping the rotation of said rotor; means for discharging a resulting supernatant from said rotor, while the precipitated cells are held on the surface of the wall; means for supplying a new liquid medium for suspending cells into said rotor; means for effecting suspension of the cells and said new liquid medium by rotating said rotor in said septa in different speeds in the liquid medium; and means for discharging the resulting new suspension through a conduit.

* * * * *